United States Patent
Kanaujia et al.

(10) Patent No.: US 8,383,166 B2
(45) Date of Patent: Feb. 26, 2013

(54) STABLE HYDROPHOBIC TOPICAL HERBAL FORMULATIONN

(75) Inventors: Parijat Kanaujia, Bangalore (IN); Rajan Balakrishnan, Chennai (IN); Jayashree Rajan, Chennai (IN); Shivaraj Basavaraj Katageri, Bangalore (IN)

(73) Assignee: Sequent Scientific Limited, Bangalore (IN)

( * ) Notice: Subject to any disclaimer, the term of this patent is extended or adjusted under 35 U.S.C. 154(b) by 126 days.

(21) Appl. No.: 12/745,858

(22) PCT Filed: Dec. 3, 2008

(86) PCT No.: PCT/IN2008/000808
§ 371 (c)(1),
(2), (4) Date: Jun. 2, 2010

(87) PCT Pub. No.: WO2009/084032
PCT Pub. Date: Jul. 9, 2009

(65) Prior Publication Data
US 2010/0255131 A1   Oct. 7, 2010

(30) Foreign Application Priority Data
Dec. 3, 2007  (IN) .......................... 2873/CHE/2007

(51) Int. Cl.
*A01N 65/00* (2009.01)
(52) U.S. Cl. ....................................... 424/725
(58) Field of Classification Search .................. None
See application file for complete search history.

(56) References Cited

U.S. PATENT DOCUMENTS 5,858,372 A    1/1999  Jacob
7,635,494 B2 * 12/2009  Chauhan et al. .............. 424/725
2005/0152996 A1  7/2005  Butler
2005/0181077 A1  8/2005  Asiedu et al.
2005/0250805 A1  11/2005  Kannan et al.
2007/0122498 A1  5/2007  Reddy et al.
2007/0231415 A1 * 10/2007  Reddy et al. .................. 424/727
2008/0269308 A1 * 10/2008  Farber .......................... 514/390

OTHER PUBLICATIONS

Gopi Radha AK, Siddha Herbs Exclusively Used in Skin Diseases, Apr. 12, 2006, http://openmed.nic.in/1467/01/skin_herbs-gopi_radha.pdf.
Agasthiyar vaitha kaviyam, 1500, Pub: Rathina Nayakar & Sons, Thirumangal vilakku press, Chenna (1952) pp. 57-58 (with TKDL English Translation).
Mohammad, Najmul Qaraabaadeen Najm-al-Ghani (20th Century AD). Munshi Nawal Kishore, Luckno, (Second Edition) 1928 AD (with TKDL English translation).
Therayar Thailavarukka Churukkam, Ed.subramanya Pandithar, Pub: Devaraja Nayagar, (1958) (With TKDL English Translation).
Kandasamy Athmarakshaamirtham, Pub: Ilakkana Achagam, Chennai (1879) (with TKDL English Translation).
Mohammad, Azam Muheet Azam, vol. IV (Part II) (19th century ADI, Marba Nizami, Kanpur.. 1895 AD).
Pandita Narahan, Rajanighantauh—Edited with Hindi Commentary by Indradeo Tripathi; krishnadas Academy, Varanasi, Edn. 2nd 1998 (with TKDL English translation).
Yamamura et al., "Antihistaminic Falvones and Aliphatic Glycosides from Mentha Spicata" Phytochemistry, vol. 48, No. 1, pp. 131-136 (1998).
Phytosterols, Phytostanols and Their Esters, New Specifications prepared at the 69th JECFA (2008).

* cited by examiner

*Primary Examiner* — Michael Meller
(74) *Attorney, Agent, or Firm* — Kramer & Amado, P.C.

(57) ABSTRACT

Disclosed herein is stable topical herbal composition, useful for the treatment of specific skin conditions, such as, including, but not limited to, psoriasis, eczema, dermatitis, inflammation, pigmentation, extreme dry skin and other skin conditions requiring therapeutic intervention, wherein the said topical herbal composition comprises, oil extract of *Wrightia tinctoria* in combination with hydrophobic excipients and other functional excipients, such as emulsifying agent, preservatives, humectant and anti oxidant.

17 Claims, No Drawings

STABLE HYDROPHOBIC TOPICAL HERBAL FORMULATIONN

TECHNICAL FIELD OF INVENTION

The present invention relates to herbal medicaments for topical application. More particularly, the invention relates to formulations comprising an herbal extract from species *Wrightia tinctoria* for the treatment of skin diseases such as psoriasis, eczema, dermatitis, inflammation, pigmentation, extreme dry skin and other skin conditions requiring therapeutic intervention. The herbal extract is oil-based and the formulation is prepared in a hydrophobic excipient base for improved stability and for enhanced results.

BACKGROUND OF INVENTION

Psoriasis is a chronic skin disease which progresses gradually, the main signs and symptoms of which are papulosquamous and itching. Psoriasis includes the presence of small elevations of the skin that may be characterized as elevated red lesions, plaques or pustules on the skin which eventually result in silvery scales. These silvery scales and plaque are the result of accelerated epidermal proliferation and the metabolic activity and proliferation of capillaries in the dermal region and the invasion of the dermis and epidermis by inflammatory cells. More specifically, the capillaries in the dermal region become tortuous and dilated as well as suffer an inflammatory reaction causing the skin to redden.

The exact mechanism which triggers the abnormal cell proliferation is not known, though it is believed that there may be biochemical stimuli and environmental factors. The severity and course of psoriasis can vary greatly depending on the individual, but in general this chronic skin condition recurs throughout the life of the individual with varying intervals of one month to many years.

The formulations to be used are limited to the most common preparations such as, solutions, creams, and salves, in which, the manner of application for the dermatherapy is practically predetermined. Historically, psoriasis has been treated topically with coal tar derivatives as well as salicylic acid with limited success. Corticosteroids and other similar drugs have been found effective for serious cases of psoriasis. Unfortunately many of these drugs produce serious side effects, and in some cases once the drugs are discontinued, the psoriasis recurs with marked exacerbation.

The *Wrightia tinctoria* R. Brown var. laevis is a tree which can grow up to 40 meters tall and has a dark gray bark. The stalk at which the leaf is attached is approximately 5-7 mm long supporting an oblong leaf blade. The tree can be commonly found growing in mountain forests and valley thickets from an elevation of 200 to 1000 meters. The tree is native to India, Indonesia, Laos, Malaysia, Myanmar, Philippines, Thailand, Vietnam, and Northern Australia. Within the regions where the plant is found the indigenous population has used the entirety of the plant for various reasons. Such uses include, utilizing the roots and leaves for the treatment of injury and cuts, the fruits to cure pulmonary tuberculosis, and extracting a blue dye from the leaves.

RELATED PRIOR ART

The process of extraction of active agent from the leaves of *Wrightia tinctoria* disclosed in U.S. Pat. No. 5,858,372 is included herein by reference. The patent entails that fresh healthy leaves are harvested from *Wrightia tinctoria* R.Br. plant and the collected leaves are cleaned with purified or filtered water and then sliced to smaller pieces. The cut leaves are combined with equal part of purified or filtered water and this combination is mixed in a mechanical churner for a specific time. The combination forms the slurry wherein the slurry is transferred to holding pans having greatest practical surface area which is exposed to light source for specific time. Concentrated slurry is obtained after the exposure of slurry to light source for specific time duration. This concentrated slurry is further processed to remove any particle aggregates such as leaf stock to obtain the medicament.

U.S. Pat. No. 5,858,372 discloses a hydrophilic ointment composition comprising of irradiated latex, extracted from the leaves of *Wrightia tinctoria*, water, urea and polyethylene glycol. The drawback of using a hydrophilic base or a hydrophilic composition is that it absorbs water from skin leaving the skin dry or dehydrated. This property can adversely affect the psoriatic condition. Moreover, aqueous herbal extracts when used with hydrophilic excipients precipitates the medicament thereby adversely affecting the stability of the formulation.

To overcome above mentioned problems associated with the use of hydrophilic topical formulation, prepared from aqueous extract of *Wrightia tinctoria*, a need for a stable hydrophobic pharmaceutical composition for the treatment of skin diseases such as psoriasis, eczema, dermatitis, inflammation, pigmentation and extreme dry skin was felt. Therefore, it is an object of the invention to provide a stable pharmaceutical composition comprising nontoxic herbal extract from species of *Wrightia tinctoria* in hydrophobic base thereby providing high storage stability, improved efficacy, devoid of any dehydrating effect as well as without any irritation to the skin.

SUMMARY OF THE INVENTION

In accordance with the above object, the invention provides a topical herbal formulation useful for treatment of specific skin diseases, wherein an oil extract is prepared and formulated using hydrophobic excipients for better stability and enhanced efficacy.

The invention further provides a process for preparation of the oil extract of the herb as well as topical herbal compositions thereof, based on pharmaceutically acceptable hydrophobic excipients.

DETAILED DESCRIPTION OF THE INVENTION

The invention will now be described in detail in connection with certain preferred and optional embodiments, so that various aspects thereof may be more fully understood and appreciated. However, these embodiments may be considered as not self-limiting, but incorporated herein as typical examples of the invention in its various and diverse options.

Thus, the present invention provides stable topical herbal composition, useful for the treatment of specific skin conditions, such as, including, but not limited to, psoriasis, eczema, dermatitis, inflammation, pigmentation, extreme dry skin and other skin conditions requiring therapeutic intervention, comprising an oil extract of *Wrightia tinctoria* in combination with hydrophobic base and other functional excipients, such as emulsifying agent, preservatives, humectant and anti oxidant.

Typically, the oil extract of *Wrightia tinctoria* is prepared as follows.

Fresh healthy leaves are harvested from *Wrightia tinctoria* R.Br. plant and the collected leaves are cleaned with purified or filtered water and then sliced to smaller pieces. The cut leaves are combined with equal part of purified or filtered water and this combination is mixed in a mechanical churner for a specific time. The combination forms the slurry wherein the slurry is transferred to holding pans having greatest practical surface area which is exposed to light source for specific time. Concentrated slurry is obtained after the exposure of slurry to light source for specific time duration. This concentrated slurry is further processed to remove any particle aggregates such as leaf stock to obtain the medicament. After the stipulated exposure to the light source, the aqueous extract is mixed with oil of natural origin. Oil of natural origin is selected from vegetable/essential oils or mineral oils selected from olive oil, Linseed oil, Rice bran oil, Safflower oil, Sesame oil, castor oil, oil of lavender, oil of almonds, or Rose oil and mostly sesame oil is used for the oil extract preparation. Even though, sesame oil is indicated as a preferred embodiment, any topically applicable oil of natural origin, such as coconut oil, palm oil, olive oil, linseed oil, Rice bran oil, Safflower oil, castor oil, oil of almonds, and Rose oil may also be used for the purpose of present invention. Mineral oils include hydrocarbon oils, liquid paraffin, lubricating oil, mineral oil (saturated paraffin oil), and white oil or essential oils such as patchouli oil, lavender or mineral origin such as petroleum jelly may be used in the preparation of the composition. In a typical composition for immediate use, the conventional ghee (butter oil) of milk origin or others such as peanut, soya or such like may also be considered for use.

In a preferred embodiment of the present invention, the oil extract of *Wrightia tinctoria* is prepared by boiling the aqueous extract of the leaves of *Wrightia tinctoria* in an amount ranging from 5 to 75% w/w; more preferably 10 to 50% and most preferably 20 to 40%. While the ratio of aqueous extract to oil may vary based on the concentration of the aqueous extract, and boiled (preferably in brass vessel) for six hours or more till the pharmaceutically acceptable consistency is reached.

One preferred embodiment comprise of boiling 30% aqueous extract with sesame oil till to obtain a pharmaceutical consistency. The consistence of the resultant oil indicating the completion of the process that can be determined by a person skilled in the art of processing oil extract of herbs.

The use of oil extract in place of aqueous extract not only increases stability of the active ingredient and the compositions thereof, but also improves the efficacy of the compositions, in view of the hydrophobic nature of the active ingredient itself, in addition to that of the excipients, which are dealt with hereinafter.

Eventhough, the oil extract itself, as such, can be used for extreme skin conditions, in view of the non-toxic nature of the herb, it is advisable and recommended to use the oil extract of *Wrightia tinctoria* in conjunction with suitable excipients. As such, the range of active ingredient, the oil extract in this context, may be from 1% to 100%. As stated earlier, the concentration of the aqueous extract and the extent of activity in the oil extract will be used to determine the percentage of the oil extract to be used in the composition.

In a preferred embodiment, the present invention describes a topical formulation comprising oil extract of *Wrightia tinctoria* in an amount ranging from 5% to 50% w/w, of the total composition, more preferably 10 to 30% w/w of the total composition, the best mode/best method being 20% concentration of the oil extract in the typical composition. The topical composition may be formulated in any form suitable for external applications. While the oil extract may as such be used in suitable dilutions, for better consumer convenience, it may be appropriate to prepare the compositions in the form of creams, gels, ointments, pastes, paint, lotion powders (by micro-encapsulation), shampoo, soaps, flakes or in the form of oil in sqeeze-out soft gel capsules. The composition may also be prepared in the form of aerosol sprays for application to the affected skin surface with the use of pharmaceutically acceptable vehicles and devices.

In another preferred embodiment, the herbal medicament of the present invention describes a topical cream formulation using a hydrophobic base. A topical formulation in hydrophobic base is particularly advantageous as it provides an emollient action and soothes the skin. Oil extract of *Wrightia tinctoria* is mixed with hydrophobic base or mixture of hydrophobic base(s), selected from following classes, Hydrophobic bases according to present invention may comprise of different bases such as Oliagenous bases, Absorption bases, Water removable base and water soluble base and mixture thereof.

Oleaginous Bases: Oleaginous bases are also termed as Hydrocarbon bases. On application to the skin, have an emollient effect, as occlusive dressing, can remain on the skin for prolonged periods of time without drying out.

Absorption Bases: Absorption bases are of two types:
(i) Those that permit the incorporation of aqueous solutions resulting in the formation of water-in-oil emulsions.
(ii) Those that are water-in-oil emulsions (syn: emulsion bases) and permit the incorporation of additional quantities of aqueous solutions.

Water Removable Bases: Water-removable bases are oil-in-water emulsions resembling creams in appearance. Because the external phase of the emulsion is aqueous, they are easily washed from skin and are often called "water-washable" bases.

Water-Soluble Bases: Water-soluble bases do not contain oleaginous components. They are completely water-washable and often referred to as "greaseless" Because they soften greatly with the addition of water; large amounts of aqueous solutions are not effectively incorporated into these bases. They mostly are used for the incorporation of solid substances.

Examples of Hydrophobic bases include but are not limited to:

Hydrocarbons: Liquid petrolatum (mineral oil, liquid paraffin, paraffin oil), White petrolatum (petroleum jelly, Vaseline), Yellow petrolatum (petroleum jelly) Squalane (perhydrosqualene, spinacane)

Silicones: Liquid polydimethylsiloxanes (dimethicone, silastic, medical grade silicone oil)

Alcohols: Lauryl alcohols (1-dodecanol, dodecyl alcohols), Myristyl alcohols (tetradecanol, tetradecyl alcohols), Cetyl alcohols (hexadecanol, ethal, palmityl alcohols), Stearyl alcohols (stenol, cetosteryl alcohols), Oleyl alcohols (ocenol) Sterols; sterol esters: Lanolin (hydrous wool fat, lanum), Anhydrous lanolin (wool fat, anhydrous lanum, agnin), Semi synthetic lanolin's Carboxylic Acids: Lauric acid, Myristic acid, palmitic acid, stearic acid, oleic acid Esters; polyesters: Cholesterol esters (stearate), Ethylene glycol monoesters, Propylene glycol monoesters, Glyceryl monoesters, Glyceryl monostearate, Sorbitol monoesters, Sorbitain monoesters, Sorbitol diesters, Sorbitan polyesters (spans, arlacels), Glyceryl tristearate, Lard, Almond oil, Corn oil, Caster oil, Cottonseed oil, Olive oil, Soyabean oil, Hydrogenated oils, Sulfated oils, Isopropyl myristate, Isopropyl palmitate. Ethers; polyethers: Polyethylene-polypropylene glycols (pluronics)

(References: Dermatological and Transdermal Formulation, Marcal Dekker, INC. New York, "Pharmaceutical Dosage Forms and Drug Delivery System", 7$^{th}$ edition, Lippincott Willams and Wilkens, Baltimore, 2000)

These hydrophobic bases, on application to the skin, produce the emollient effect, protect against the escape of moisture, are effective as occlusive dressings, can remain on the skin for long periods without drying out. These properties are particularly advantageous when treating psoriasis conditions.

Further hydrophobic formulation comprises of surfactant(s), preservative (s) selected from one or more parabens such as sodium or potassium methyl, ethyl or Propyl paraben. Combination of paraben derivatives are used as preservatives. Humectant(s) such as Propylene glycol and anti-oxidants such as butylated hydroxyl toluene and butylated hydroxyl anisole.

The herbal medicament/topical formulation of the present invention may optionally comprise one or more herbal extracts/ingredients derived from Datura alba, Neem, Turmeric, Aloe vera, Oatmeal and Jojoba.

Accordingly, in a typical embodiment, the herbal medicament of the present invention comprises 20% of the oil extract of *Wrightia tinctoria* together with hydrophobic base; and other functional excipients such as emulsifying agent, preservatives, humectant and antioxidant.

According to present invention the most preferred process of manufacturing topical formulation comprises of the following steps:
 a) heating oil extract of *Wrightia tinctoria* with hydrophobic base by maintaining the temperature in the range of 70 to 80° C., dissolving anti oxidant;
 b) dissolving emulsifying agent, preservative, humectant in Purified water, followed by heating the mixture by maintaining the temperature in the range of 70 to 80° C.;
 c) adding the mixture obtained in step (b) to the oil phase obtained in step (a) and maintaining the mixture at a temperature range 70 to 80° C.;
 d) homogenizing the mixture & subsequently cooling the emulsion to obtain a stable consistent cream.

The herbal medicament from the plant extract, *Wrightia tinctoria* prepared according to the above process is preferably applied topically to affected skin area.

According to present invention the topical formulation could be either ointment or cream. The most preferred form of topical formulation according to present invention is in the form of cream as they find primary application in topical skin products.

Pharmaceutical creams are semisolid preparations containing one or more medicinal agents dissolved or dispersed in either
  Water-in-oil emulsion or
  Oil-in-water emulsion or
  Water-washable base.
  Advantages of Using Cream Bases:
  Many physicians and patients prefer creams to ointments because they are easier to spread & remove.
  Properly designed creams are elegant drug delivery system, pleasing in both appearance and feel post application.
  Creams are non greasy and easy to rinse.
  They are good for most topical purpose and are considered particularly suited for application to oozing wounds/psoriasis.

DETAILED DESCRIPTION OF PREFERRED EMBODIMENTS

Hydrophobic bases employed in the present invention include:

Petrolatum: Petrolatum is a pale yellow to yellow-colored, translucent, soft unctuous mass. It is odorless, tasteless, and not more than slightly fluorescent by daylight, even when melted.

Petrolatum is a purified mixture of semisolid saturated hydrocarbons having the general formula $C_nH_{2n+2}$, and is obtained from petroleum. The hydrocarbons consist mainly of branched and un-branched chains although some cyclic alkanes and aromatic molecules with paraffin side chains may also be present.

Petrolatum is mainly used in topical pharmaceutical formulations as an emollient-ointment base; it is poorly absorbed by the skin. Petrolatum is also used in creams and transdermal formulations and as an ingredient in lubricant formulations for medicated confectionery together with mineral oil. In the present invention the concentration range used varies from 4% to 25% w/w.

(Reference: Handbook of Pharmaceutical Excipients $5^{th}$ Edition)

Stearic Acid: Stearic acid is a hard, white or faintly yellow-colored, somewhat glossy, crystalline solid or a white or yellowish white powder. It has a slight odor and taste suggesting tallow.

Stearic acid occurs as a mixture of stearic acid ($C_{18}H_{36}O_2$) and palmitic acid ($C_{16}H_{32}O_2$). In the USPNF 21, the content of stearic acid is not less than 40.0% and the sum of the two acids is not less than 90.0%.

In topical formulations, stearic acid is used as an emulsifying and solubilizing agent. In the present invention the concentration range used varies from 1% to 20% w/w (Reference: Handbook of Pharmaceutical Excipients $5^{th}$ Edition)

Cetyl Alcohol: Cetyl alcohol occurs as waxy, white flakes, granules, cubes, or castings. It has a faint characteristic odor and bland taste.

Cetyl alcohol, used in pharmaceutical preparations, is a mixture of solid aliphatic alcohols comprising mainly 1-hexadecanol ($C_{16}H_{34}O$).

In lotions, creams, and ointments Cetyl alcohol is used because of its emollient, water-absorptive, and emulsifying properties. It enhances stability, improves texture, and increases consistency. The emollient properties are due to absorption and retention of Cetyl alcohol in the epidermis, where it lubricates and softens the skin while imparting a characteristic 'velvety' texture.

Cetyl alcohol is also used for its water absorption properties in water-in-oil emulsions. For example, a mixture of petrolatum and Cetyl alcohol (19:1) will absorb 40-50% of its weight of water. Cetyl alcohol has also been reported to increase the consistency of water-in-oil emulsions.

In oil-in-water emulsions, Cetyl alcohol is reported to improve stability by combining with the water-soluble emulsifying agent (Sodium lauryl sulphate). The combined mixed emulsifier produces a close packed, monomolecular barrier at the oil-water interface which forms a mechanical barrier against droplet coalescence. In the present invention the concentration range used varies from 2% to 10% w/w.

(Reference: Handbook of Pharmaceutical Excipients $5^{th}$ Edition)

Liquid Paraffin: Mineral oil is a transparent, colorless, viscous oily liquid, without fluorescence in daylight. It is practically tasteless and odorless when cold, and has a faint odor of petroleum when heated.

Mineral oil is used primarily as an excipient in topical pharmaceutical formulations, where its emollient properties are exploited as an ingredient in ointment bases. It is additionally used in oil-in-water emulsions, as a solvent, and as a lubricant in capsule and tablet formulations, and to a limited extent as a mold-release agent for cocoa butter suppositories. In the present invention the concentration range used varies from 1% to 32% w/w. (Reference: Handbook of Pharmaceutical Excipients $5^{th}$ Edition)

Hard Paraffin: Paraffin is an odorless and tasteless, translucent, colorless, or white solid. It feels slightly greasy to the touch and may show a brittle fracture. Microscopically, it is a mixture of bundles of microcrystals. Paraffin burns with a luminous, sooty flame. When melted, paraffin is essentially without fluorescence in daylight; a slight odor may be apparent.

Paraffin is mainly used in topical pharmaceutical formulations as a component of creams and ointments. In ointments, it may be used to increase the melting point of a formulation or to add stiffness. In the present invention the concentration range used varies from 1% to 14% w/w. (Reference: Handbook of Pharmaceutical Excipients 5$^{th}$ Edition)

Bees Wax: Bees wax, also called as white wax consists of tasteless, white or slightly yellow-colored sheets or fine granules with some translucence. Its odor is similar to that of yellow wax but is less intense.

Bees wax consists of 70-75% of mixture of various esters of straight chain monohydric alcohols with even numbered carbon chains from $C_{24}$ to $C_{36}$ esterified with straight chain acids. These straight chain acids also have even numbers of carbon atom up to $C_{36}$ together with some $C_{18}$ hydroxy acids. The chief ester is myricyl palmitate. In the present invention the concentration range used varies from 1% to 5% w/w. (Reference: Handbook of Pharmaceutical Excipients 5$^{th}$ Edition)

Sodium Lauryl Sulfate: Sodium lauryl sulfate consists of white or cream to pale yellow-colored crystals, flakes, or powder having a smooth feel, a soapy, bitter taste, and a faint odor of fatty substances. Sodium lauryl sulfate is an anionic surfactant employed in a wide range of non parenteral pharmaceutical formulations and cosmetics. In the present invention the concentration range used varies from 0.5% to 2.5% w/w (Reference: Handbook of Pharmaceutical Excipients 5$^{th}$ Edition)

Propylene Glycol: Propylene glycol is a clear, colorless, viscous, practically odorless liquid with a sweet, slightly acrid taste resembling that of glycerin.

Propylene glycol is used in cosmetics and in the food industry as a carrier for emulsifiers and as a vehicle for flavors in preference to ethanol, since its lack of volatility provides a more uniform flavor. In the present invention the concentration range used varies from 5% to 20% w/w.

Preservatives: Antimicrobial preservatives are used to prevent or inhibit the growth of microorganisms, this could present a risk of infection or degradation of the medicinal product. These microorganisms may proliferate during normal storage conditions or use of the product by the patient, particularly in multidose preparations.

The preservatives used in the present invention include but are not limited to: Sodium methyl paraben, Sodium Propyl paraben, Benzyl alcohol, Benzoic acid, Chlorocresol, Bronopol etc.

In the present invention, sodium methyl paraben & sodium propyl paraben are used as antimicrobial preservatives in the concentration range from 0.02% to 0.3% w/w & 0.01 to 0.6 respectively. (Reference: Handbook of Pharmaceutical Excipients 5$^{th}$ Edition)

Antioxidants: Antioxidants are used to reduce the oxidation of active substances and excipients in the finished product. However antioxidants are not used to disguise poorly formulated products or inadequate packaging. Oxidative degradation can be accelerated by light and by the presence of mineral impurities, due to the formation of free radicals. Since the excipients used in the present invention (White petrolatum) may oxidize on exposure to light, to inhibit this, anti oxidant is added in the formulation. The antioxidants used in the present invention include but are not limited to the following: Butylated Hydroxy Anisole, Butylated Hydroxy Toulene, Ascorbic acid, D-α-tocopherol etc.

In the present invention, Butylated hydroxy anisole is used as anti oxidant in the concentration range from 0.0075% to 0.1% w/w. (Reference: Handbook of Pharmaceutical Excipients 5$^{th}$ Edition)

The following examples, which include preferred embodiments, will serve to illustrate the practice of this invention, it being understood that the particulars shown are by way of example and for purpose of illustrative discussion of preferred embodiments of the invention.

EXAMPLES

Example 1

A herbal formulation comprising following composition was prepared.

| Ingredients | Quantity/100 g |
|---|---|
| *Wrightia tinctoria* oil extract | 20 g |
| Stearic acid | 4 g |
| Cetyl alcohol | 4 g |
| White soft parafin | 22 g |
| Sodium lauryl sulphate | 1 g |
| Sodium methyl suphate | 0.025 g |
| Sodium propyl paraben | 0.015 g |
| Propylene glycol | 5 g |
| Butylated Hydroxy toluene | 0.01 g |
| Purified water | 44 g |

Example 2

A herbal formulation comprising following composition was prepared.

| Ingredients | Quantity |
|---|---|
| *Wrightia tinctoria* oil extract | 20 g |
| Bees wax | 35 g |
| Borate sodium salt | 1 g |
| Sodium methyl suphate | 0.025 g |
| Sodium propyl paraben | 0.015 g |
| Butylated Hydroxy toluene | 0.01 g |
| Purified water | 49 g |

Example 3

A herbal formulation comprising following composition was prepared.

| Ingredients | Quantity |
|---|---|
| *Wrightia tinctoria* oil extract | 20 g |
| Liquid parafin | 19 g |
| Bees wax | 30 |
| Borate sodium salt | 1 g |
| Sodium methyl suphate | 0.025 g |
| Sodium propyl paraben | 0.015 g |
| Butylated Hydroxy toluene | 0.01 g |
| Purified water | 30 g |

Example 4

| Ingredients | Quantity/100 g |
| --- | --- |
| *Wrightia tinctoria* oil extract | 20 g |
| Stearic acid | 2 g |
| Pegoxol 7 Stearate | 10 g |
| White soft parafin | 18 g |
| Sodium methyl suphate | 0.025 g |
| Sodium propyl paraben | 0.015 g |
| Propylene glycol | 5 g |
| Butylated Hydroxy toluene | 0.01 g |
| Purified water | 44.95 g |

The rate of healing of a typical conventional psoriasis on comparably equivalent body location of the same target patient has been undertaken, using external preparation based on hydrophilic as well as hydrophobic excipients. It was observed that, while the *Wrightia tinctoria* based composition gave good response in rate of healing compared to placebo, the rate of healing caused by the application of hydrophobic material was proved to be superior and faster to that of the hydrophilic materials.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A stable topical herbal composition for treating a skin condition selected from the group consisting of psoriasis, eczema, dermatitis, inflammation, and extreme dry skin, comprising a therapeutically effective amount of an aqueous extract of *Wrightia tinctoria* in combination with a hydrophobic base and at least one functional excipient,
    wherein the aqueous extract of *Wrightia tinctoria* is prepared by boiling the aqueous extract of *Wrightia tinctoria* with a topically compatible oil of natural origin selected from the group consisting of olive oil, Linseed oil, Rice bran oil, Safflower oil, Sesame oil, Castor oil, Lavender oil, Almond oil, Rose oil and mixtures thereof.

2. The topical herbal composition as in claim 1, wherein the oil of natural origin is Sesame oil.

3. The topical herbal composition as in claim 1, wherein the aqueous extract of *Wrightia tinctoria* is prepared by boiling a mixture of the aqueous extract of *Wrightia tinctoria* and the topically compatible oil of natural origin, wherein the concentration of said aqueous extract of the *Wrightia tinctoria* in said mixture is between 10% and 50% w/w.

4. The topical herbal composition as in claim 1, wherein the concentration of the aqueous extract of the *Wrightia tinctoria* in said mixture is between 20% and 40% w/w.

5. The topical herbal composition as in claim 4, wherein the concentration of said aqueous extract of the *Wrightia tinctoria* in said mixture is about 30% w/w.

6. The topical herbal composition as in claim 1, wherein the hydrophobic base is selected from the group consisting of petrolatum, soft paraffin, hard paraffin, liquid praraffin, petroleum jelly, yellow bees wax, white bees wax, shea butter, permaceti, anionic emulsifying wax, and mixtures thereof.

7. The topical herbal composition as in claim 6, wherein the hydrophobic base further comprises white bees wax, stearic acid, Cetyl alcohol, or mixtures thereof.

8. The topical herbal composition as in claim 1, wherein the composition further comprises one or more herbal extracts/ingredients derived from Datura alba, Neem, Turmeric, Aloe vera, Oatmeal and Jojoba.

9. The topical herbal composition as in claim 1, wherein the functional excipient is at least one excipient selected from the group consisting of an emulsifying agent, a preservative, a humectant, an anti-oxidant, and a mixture thereof.

10. The topical herbal composition as in claim 9, wherein the emulsifying agent is an alkali metal salt of lauryl sulphate or a borate.

11. The topical herbal composition as in claim 10, wherein the emulsifying agent is sodium lauryl sulphate.

12. The topical herbal composition as in claim 9, wherein the preservative is at least one compound selected from the group consisting of alkali metal salts of methyl paraben, ethyl paraben, and propyl paraben.

13. The topical herbal composition as in claim 9, wherein the humectant is propylene glycol.

14. The topical herbal composition as in claim 9, wherein the antioxidant is butylated hydroxyl toluene.

15. A process for preparation of a topical herbal composition according to claim 1, wherein said composition is a cream, prepared by a process comprising:
    a) heating the aqueous extract of *Wrightia tinctoria* with a hydrophobic base and dissolving an antioxidant therein to obtain an oil phase;
    b) dissolving an emulsifying agent, preservative, humectant, or a mixture thereof in purified water to obtain an aqueous mixture, followed by heating the aqueous mixture;
    c) adding the aqueous mixture obtained in step (b) to the oil phase obtained in step (a) under continuous stirring to obtain an emulsion and maintaining the emulsion at a temperature range; and
    d) homogenizing the emulsion and subsequently cooling the homogenized emulsion to obtain the topical herbal composition of claim 1.

16. The process as in claim 15, wherein steps (a), (b), and (c) are performed at a temperature between 70 degrees centigrade and 80 degrees centigrade.

17. A stable topical herbal composition for treating a skin condition selected from the group consisting of psoriasis, eczema, dermatitis, inflammation, and extreme dry skin, consisting essentially of a therapeutically effective amount of an aqueous extract of *Wrightia tinctoria* in combination with a hydrophobic base and at least one functional excipient,
    wherein the aqueous extract of *Wrightia tinctoria* is prepared by boiling the aqueous extract of *Wrightia tinctoria* with a topically compatible oil of natural origin selected from the group consisting of olive oil, Linseed oil, Rice bran oil, Safflower oil, Sesame oil, Castor oil, Lavender oil, Almond oil, Rose oil and mixtures thereof.

* * * * *